United States Patent [19]

Endo et al.

[11] Patent Number: 5,142,050

[45] Date of Patent: Aug. 25, 1992

[54] AROMATIC ISOCYANURATE COMPOUND

[75] Inventors: Takeshi Endo, Kanagawa; Yoko Nambu, Tokyo, both of Japan

[73] Assignee: Asahi Denka Kogyo K.K., Tokyo, Japan

[21] Appl. No.: 662,347

[22] Filed: Feb. 26, 1991

[30] Foreign Application Priority Data

Mar. 12, 1990 [JP] Japan .................................. 2-62428

[51] Int. Cl.⁵ .......................................... C07D 251/34
[52] U.S. Cl. .................................................. 544/221
[58] Field of Search ........................................ 544/221

[56] References Cited

U.S. PATENT DOCUMENTS 4,243,570 1/1981 Mark et al. ..................... 260/30.2

FOREIGN PATENT DOCUMENTS 0076067 4/1983 European Pat. Off. .

OTHER PUBLICATIONS

Victor et al., Chemical Abstracts, vol. 95, entry 26127h (1981).
Bukac et al., Chemical Abstracts, vol. 103, entry 123978c (1985).
Koyama et al, Chemical Abstracts, vol. 110 entry 114094d (1989).
Journal of The American Chemical Society, vol. 78, 1956, Gaston, Pa., pp. 4911–4914, I. C. Kogon, "New Reactions of Phenyl Isocyanate and Ethyl Alcohol".
Chemical Abstracts, vol. 103, No. 16, Oct. 21, 1985, Columbus, Ohio; Abstract No. 123978C, Z. Bukac et al, "Alkaline Polymerization of 6-Caprolactam, LVII".

*Primary Examiner*—John M. Ford
*Attorney, Agent, or Firm*—Flynn, Thiel, Boutell & Tanis

[57] ABSTRACT

A novel tri-substituted triphenyl isocyanurate is defined by the following formula and useful as a crosslinking agent for resins.

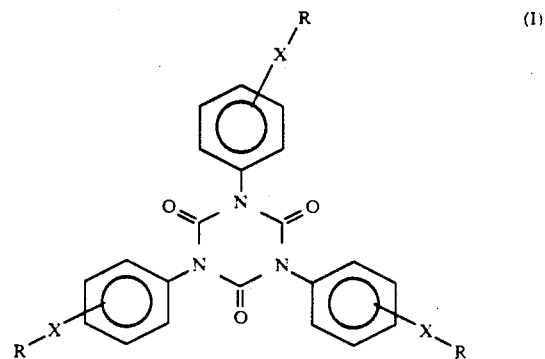

wherein X represents —O— or —COO—; and R represents a hydrogen atom, a straight-chain or branched alkyl group having 1 to 10 carbon atoms, which may be either unsubstituted or substituted with a hydroxyl group, an aryl group or an $R'_3Si$ group (wherein a plurality of R' groups may be the same or different from each other and each represents a straight-chain or branched alkyl group having 1 to 10 carbon atoms or a phenyl group), except when X is —O— and R is $CH_3$.

4 Claims, No Drawings

AROMATIC ISOCYANURATE COMPOUND

BACKGROUND OF THE INVENTION

The present invention relates to a novel reactive group-substituted triphenyl isocyanurate compound which is useful as a heat-resistant crosslinking agent for epoxy resins, polyesters, polyethers and polyurethanes and which exhibits a liquid crystal-like high orientation as such or as a polymeric derivative thereof.

PRIOR ART

An aromatic isocyanurate structure formed by the trimerization of an organic aromatic isocyanate has been known to improve various properties of polyurethane or coating materials such as heat resistance, flame retardance, chemical resistance and film-forming properties. However, the introduction of an isocyanurate structure, which contains an ether or ester group and is expected to exhibit various excellent characteristics, into a synthetic polymer at an arbitrary ratio has been so difficult that only the synthesis of polyurethane from an aromatic diisocyanate and a polyol having various groups through trimerization has been conducted. Further, it is nearly impossible to introduce an aromatic isocyanurate into a polyester, polyether or polyurethane at an arbitrary ratio.

These problems can be solved by using an aromatic isocyanurate derivative having various reactive groups as a monomer or a crosslinking agent in the synthesis of a polymer.

However, known aromatic isocyanurates having a reactive group are so few that they include, at the most, trimers of aromatic diisocyanate such as tolylene diisocyanates and diphenylmethane diisocyanate and trimethylsilyl derivatives thereof (See Tanimoto et al., Japanese Patent Publication No. 34823/1970), triaryl isocyanurate derivatives having an azidosulfonyl group [see H. Ulrich, U.S. Pat. No. 3562269 (1971)] and triphenyl isocyanurate derivatives having an allyloxy or glycidyloxy group (see Japanese Patent Application No. 60265/1989).

Meanwhile, no studies have been reported on the properties of a substituted aromatic isocyanurate, although A. Usanmaz ascertained by X-ray diffractometry that triphenyl isocyanurate has a layered structure in parallel to the cyanuric ring thereof [see Acta Cryst., B35, 1117(1979)].

SUMMARY OF THE INVENTION

The inventors of the present invention have made intensive studies directed to the synthesis of novel reactive aromatic isocyanurates from several substituted aromatic isocyanates through selective trimerization, thus accomplishing the present invention.

Namely, the present invention relates to a tri-substituted triphenyl isocyanurate represented by the following general formula (I):

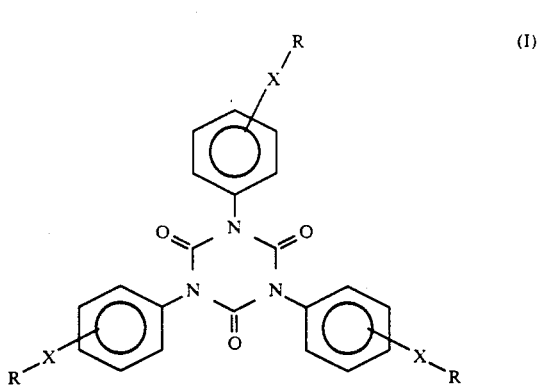

wherein X represents —O— or —COO—; and R represents a hydrogen atom, a straight-chain or branched alkyl group having 1 to 10 carbon atoms, which may be either unsubstituted or substituted with a hydroxyl group, an aryl group or an $R'_3Si$ group (wherein the plurality of R' groups may be the same or different from each other and each represents a straight-chain or branched alkyl group having 1 to 10 carbon atoms or a phenyl group), excepting the case wherein X is —O— and R is $CH_3$.

Now, the isocyanurate compound of the present invention will be described in more detail.

According to the present invention, the substituents of the tri-substituted triphenyl isocyanurate represented by the general formula (I) may be each present at any of meta, para and ortho positions.

The tri-substituted triphenyl isocyanurate represented by the general formula (I) according to the present invention is prepared through the selective trimerization of an isocyanate represented by the following general formula (II):

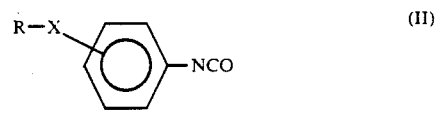

wherein X and R are each as defined above with respect to the formula (I).

Among the isocyanates represented by the general formula (II), which are each a raw material of the novel isocyanurate compound according to the present invention, an isocyanate compound of the formula (II), wherein X is —O— or —COO— and R is a straight-chain or branched alkyl group having 1 to 10 carbon atoms, which is unsubstituted or substituted with a hydroxyl group, or an aryl group, can be prepared from a corresponding substituted aniline derivative. The alkyl group defined with respect to R includes $CH_3$, $C_2H_5$, n-$C_3H_7$, i-$C_3H_7$, $C_4H_9$, $C_5H_{11}$, $C_6H_{13}$, $C_7H_{15}$ and $C_8H_{17}$ groups. The aryl group defined with respect to R includes substituted and unsubstituted phenyl and naphthyl groups. However, a compound represented by the formula (II), wherein X is —O— and R is $CH_3$, is excluded.

Among the isocyanates represented by the general formula (II), which are each a raw material of the novel isocyanurate compound according to the present invention, an isocyanate compound of the formula (II), wherein X is —O— or —COO— and R is an $R'_3Si$ group (wherein R' is as defined above) can be prepared from a corresponding hydroxyl- or carboxyl-substituted aniline according to the method of W. Mormann et al. [see Synthesis, 990 (1988)]. The group defined with respect to R' includes $CH_3$, $C_2H_5$, $n-C_3H_7$, $i-C_3H_7$, $n-C_4H_9$, $t-C_4H_9$ and phenyl groups. The three R' groups may either be the same or composed of two or three of the groups described above.

Methods of aromatic isocyanurate synthesis include the trimerization of an aromatic isocyanate [see I. C. Kogan, J. Am. Chem. Soc., 78, 4911 (1956), J. I. Jones et al., J. Chem. Soc., 4392 (1957), S. L. Shapiro et al., J. Org. Chem. 26, 1600 (1963), and S. Herbstman, J. Org. Chem., 30, 1259 (1965)]. However, we can find no example of the trimerization of a substituted aromatic isocyanate as described above, nor that with respect to other preparation processes of the trimer thereof. Particularly, the conversion of an isocyanate compound having a reactive substituent as represented by the above general formula (II) into an aromatic isocyanurate necessitates the use of a selective trimerization catalyst. The inventors of the present invention have already found that cesium fluoride and tetraalkylammonium fluoride catalysts exhibit high selectivity and high activity for trimerization. The use of such a catalyst is also preferable in the present invention. Further, other trimerization catalysts such as tertiary amines may be used.

The isocyanurate compound of the present invention having an $R'_3Si$ group (wherein R' is as defined above) can be easily converted into a novel OH- or COOH- substituted aromatic isocyanurate compound by acid hydrolysis.

The novel aromatic isocyanurate having a reactive substituent according to the present invention permits the introduction of an aromatic isocyanurate skeleton into a general-purpose or engineering plastic such as a polyester, polyurethane or polyether at an arbitrary ratio through various linkages by virtue of its reactivity. The introduction of such a skeleton improves these polymers with respect to heat resistance, flame retardance, chemical resistance and film-forming properties.

The substituted aromatic isocyanurate according to the present invention has been ascertained to exhibit high orientability owing to the molecular interaction thereof, so that the utilization thereof as a novel liquid crystal compound is expected.

EXAMPLES

The present invention will now be described in more detail by referring to the following Examples, through the present invention is not limited to them.

Example 1

0.61 g (4.0 mmol) of cesium fluoride was weighed into a flask and dried under a reduced pressure at 130° C. for 30 minutes. 41.4 g (0.20 mol) of 4-trimethylsilyloxyphenyl isocyanate was added into the flask and the contents were vigorously stirred at 130° C. for 5 minutes. The formed solid was dissolved in methylene chloride and the catalyst was filtered out. The solvent was distilled off under a reduced pressure to give 41.2 g (yield: 98.0% of tris(4-trimethylsilyloxyphenyl) isocyanurate (hereinafter referred to as "TSOPI").

Results of Analysis mp: 202° to 204° C.

IR(KBr): 1720 $cm^{-1}$ (isocyanurate), 1603 $cm^{-1}$ (phenyl), 1270, 1250 $cm^{-1}$ (silyl ether).

$^1H$-NMR($CKCl_3$): 0.25 ppm (s, 27H, $Me_3Si$), 6.8 to 7.3 ppm (m, 12H, phenylene).

As shown above, the spectral data corresponded to that of TSOPI.

Example 2

10 ml of 1N hydrochloric acid was added to 200 ml of a solution of 26.5 g (0.20 mol) of the TSOPI prepared in Example 1 in methanol. The obtained mixture was reacted at a room temperature for 30 minutes and the solvent removed to give 24.5 g of a solid. This solid (crude crystal) was dissolved in 100 ml of methanol and 30 ml of chloroform was then gradually added to the obtained solution to give 21.5 g of tris(4-hydroxyphenyl) isocyanurate (hereinafter referred to as "THPI") at a yield of 81.0%.

Results of analysis mp: >300° C.

IR(KBr): 3400 $cm^{-1}$ (hydroxyl group), 1695 $cm^{-1}$ (isocyanurate).

$^1H$-NMR(d-acetone) δ: 6.8 to 7.5 ppm (m, 12H, phenylene).

elemental analysis: as $C_{21}H_{15}N_3O_6$.

|  | H | C | N |
|---|---|---|---|
| calculated (%) | 3.73 | 62.22 | 10.37 |
| found (%) | 3.64 | 61.56 | 9.95 |

As shown above, the spectral data and results of the elemental analysis corresponded that of THPI.

Further, the THPI was dissolved in either ethyl acetate or N,N dimethylacetamide (DMAc) and the obtained solution was cast on a glass plate. The solvent was gradually evaporated off to give a transparent heat-resistant thin film.

Example 3

9 g (0.022 mol) of the THPI prepared in Example 2 and 11.3 g (0.033 mol) of bisphenol A diglycidyl ether (epoxy equivalent: 183) were sufficiently dissolved in 30 ml of DMAc and the obtained solution was heated at 150° C. for one hour and then at 160° C. for 2 hours. The IR absorption (905 $cm^{-1}$) of to an epoxy group completely disappeared and a transparent resin film was formed. When this film was cooled to a room temperature and then gradually heated to 150° C. in a state in which it was sandwiched between two glass plates, high orientation was observed.

Example 4

2.9 g (7.2 mmol) of THPI and 5.9 ml (64 mmol) of propyl bromide were dissolved in 100 ml of acetone, followed by the addition of 3.1 g (22 mmol) of potassium carbonate. The obtained mixture was refluxed for 16 hours and distilled to remove the solvent. The residue was dissolved in ethyl acetate and the obtained solution was washed with a 5% aqueous solution of sodium carbonate. The organic layer was dried over magnesium sulfate and distilled to remove the solvent, thus giving 1.2 g (yield: 32.7%) of tris(4-propyloxyphenyl) isocyanurate (hereinafter referred to as "TPrPI"). This product can be purified by recrystallization from isopropanol.

mp: 205° C.

IR(KBr): 1715 $cm^1$ (isocyanurate).

1H-NMR (CDCl₃)δ: 1.03 ppm (t, 9H, Me), 1.81 ppm (d-t, 6H, CH₂), 3.94 ppm (t, 6H, CH₂O), 6.9 to 7.4 ppm (m, 12H, phenylene).

elemental analysis: as $C_{30}H_{33}N_3O_6$.

|  | H | C | N |
| --- | --- | --- | --- |
| calculated (%) | 6.26 | 67.78 | 7.90 |
| found (%) | 6.40 | 67.59 | 7.75 |

As shown above, the spectral data and the results of the elemental analysis corresponded to that of TPrPI.

Further, the thermal behavior of the TPrPI was examined by differential thermal analysis (DSC). In the second and subsequent heating steps, an exothermic peak of 115° C. and endothermic peaks of 197° C., 209° C. and 224° C. were observed. Furthermore, in the polarization microscopic examination of the TPrPI, a liquid crystal-like orientation image was observed among the above endothermic peaks.

Example 5

0.61 g (4.0 mmol) of cesium fluoride was weighed into a flask and dried under a reduced pressure at 130° C. for 30 minutes, followed by the addition of 41.4 g (0.20 mol) of 4-trimethylsilyloxyphenyl isocyanate and 27.0 ml (0.20 mmol) of phenyl glycidyl ether, and the contents were vigorously stirred at 130° C. for one hour. The trimerization and the addition of the silyl ether to the epoxy group proceeded quantitatively to give a triphenyl isocyanurate having phenoxy and trimethylsilyloxy groups. This compound can be easily converted into a triphenyl isocyanurate substituted by a secondary alcohol by acid hydrolysis.

Results of analysis

IR(KBr): 1710 cm⁻¹ (isocyanurate), 1275, 1255 cm⁻¹ (silyl ether).

¹H-NMR (CDCl₃): 0.17 (s, 9H, Me₃Si), 3.9 to 4.5 (m, 5H, CH, CH₂), 6.8 to 7.6 ppm (m, 9H, phenyl, phenylene).

As shown above, the spectral data corresponded to that of a triphenyl isocyanurate having phenoxy and trimethylsilyloxy groups.

Example 6

4 ml (4 mmol) of a 1M solution of tetrabutylammonium fluoride in THF was added to 50.1 g (0.20 mol) of 4-trimethylsilyloxycarbonylphenyl isocyanate. When the obtained mixture was heated to 70° C. and vigorously stirred, the system solidified after 30 seconds. Thereafter, the system was heated for one minute to give a solid, which was washed with anhydrous ether to give 45.6 g (yield: 91.0%) of tris(4-trimethylsilyloxycarbonylphenyl) isocyanurate (hereinafter referred to as "TSCPI").

Results of analysis mp: 227° to 229° C.

IR:(KBr): 1720 cm⁻¹ (isocyanurate), 1705 cm⁻¹ (ester), 1310, 1295 cm⁻¹ (silyl ester).

¹H-NMR(CDCl₃): 0.40 ppm (s, 27H, Me₃Si), 7.4 to 7.6, 8.1 to 8.3 ppm (m, 12H, phenylene).

As shown above, the spectral data corresponded to that of TSCPI.

Example 7

18 ml of 1N hydrochloric acid was added to 200 ml of a solution of 22.5 g (0.03 mol) of the TSCPI prepared in Example 6 in acetone and the obtained mixture was reacted at room temperature for 10 minutes. The reaction mixture was removed from the solvent and washed with water to give 12.7 g (yield: 86.5%) of a solid. This solid (crude crystal) was dissolved in 100 ml of methanol, followed by the gradual addition of 30 ml of chloroform, to give 8.3 g of tris(4-carboxylphenyl)isocyanurate (hereinafter referred to as "TCPI").

Results of analysis mp: >300° C.

IR(KBr): 3000 to 3500 cm⁻¹ (carboxyl), 1696 to 1720 cm⁻¹ (isocyanurate, carboxyl).

¹H-NMR(d-DMSO)δ: 7.5 to 7.8, 8.0 to 8.3 ppm (m, 12H, phenylene).

As shown above, the spectral data and the results of the elemental analysis corresponded to that of TCPI.

Example 8

0.61 g (4.0 mmol) of cesium fluoride was weighed into a flask and dried under a reduced pressure at 130° C. for 30 minutes, followed by the addition of 35.4 g (0.20 mol) of 4-methoxycarbonylphenyl isocyanate. The contents were vigorously stirred at 130° C. for one minute and the formed solid was dissolved in methlene chloride. The catalyst and a by-product (dimer) were filtered out and the solvent was distilled off under a reduced pressure to give 30.4 g (yield: 85.8%) of tris(-4methoxycarbonylphenyl) isocyanurate (hereinafter referred to as "TMCPI").

Results of anaylsis mp: >320° C.

IR(KBr): 2955 cm⁻¹ (methyl), 1718 cm⁻¹ (isocyanurate).

¹H-NMR (CDCl₃)δ: 3.95 ppm (s, 9H, Me), 7.4 to 7.7, 8.1 to 8.4 ppm (m, 12H, phenylene).

elemental analysis: as $C_{27}H_{21}N_3O_9$.

|  | H | C | N |
| --- | --- | --- | --- |
| calculated (%) | 3.98 | 61.02 | 7.91 |
| found (%) | 3.90 | 60.95 | 7.93 |

As shown above, the spectral data and the results of the elemental analysis corresponded to that of TMCPI.

We claim:

1. A tri-substituted triphenyl isocyanurate of general formula (I)

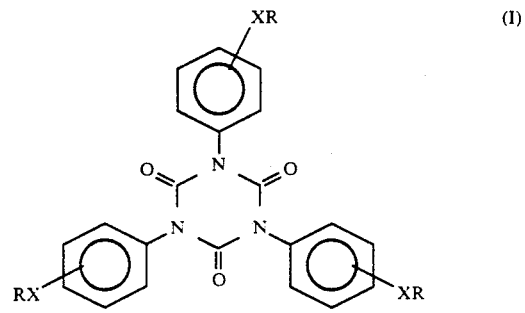

wherein X is —COO— and R is hydrogen, a straight-chain or branched alkyl group having 1 to 10 carbon atoms, which may be either unsubstituted or substituted with a hydroxyl group, phenyl, napthyl or R'$_3$Si, wherein R' are all the same or different from each other and each represents a straight-chain or branched alkyl group having 1 to 10 carbon atoms or a phenyl group.

2. A tri-substituted triphenyl isocyanurate of general formula (I)

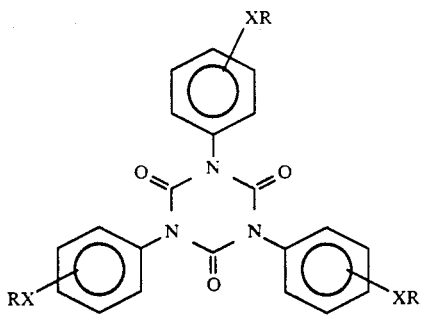

wherein X is —O— or —COO— R is R'$_3$Si, wherein R' are all the same or different from each other and each represents a straight-chain or branched alkyl group having 1 to 10 carbon atoms or a phenyl group.

3. The tri-substituted triphenyl isocyanurate of claim 2, wherein said isocyanurate is tris(4-trimethylsilyloxyphenyl) isocyanurate.

4. The tri-substituted triphenylisocyanurate of claim 1, wherein said isocyanurate is tris(4-trimethylsilyloxycarbonylphenyl) isocyanurate.

* * * * *